United States Patent [19]

Braun et al.

[11] Patent Number: 5,157,380
[45] Date of Patent: Oct. 20, 1992

[54] OVERHEATED ELECTRICAL INSULATION DETECTOR

[75] Inventors: J. M. Braun, Toronto; D. F. Mullins, Burlington, both of Canada

[73] Assignee: Electric Power Research Institute, Inc., Palo Alto, Calif.

[21] Appl. No.: 657,446

[22] Filed: Feb. 15, 1991

[51] Int. Cl.$^5$ .............................................. G08B 21/00
[52] U.S. Cl. ...................................... 340/647
[58] Field of Search ............... 73/865.9, 28.01, 31.03; 340/632, 647, 648

[56] References Cited

U.S. PATENT DOCUMENTS

| | | | |
|---|---|---|---|
| 4,364,032 | 12/1982 | Narato et al. | 340/647 |
| 4,381,922 | 5/1983 | Frey et al. | 73/23.31 |
| 4,384,925 | 5/1983 | Stetter et al. | 340/632 |
| 4,436,699 | 3/1984 | Narato et al. | 340/647 |
| 4,986,526 | 1/1990 | Ratfisch | 340/632 |
| 5,053,754 | 10/1991 | Wong | 340/632 |

FOREIGN PATENT DOCUMENTS 3123279  12/1982  Fed. Rep. of Germany ...... 340/632

OTHER PUBLICATIONS

Miller, "Early Warning Fire Detection Using Low Level CO Monitors", Fourth WVA Conference on Coal Mining Electrotechnology, Morgantown, W.V., USA, (2-4 Aug. 1978).

*Primary Examiner*—Robert Raevis
*Attorney, Agent, or Firm*—Flehr, Hohbach, Test, Albritton & Herbert

[57] ABSTRACT

A method and apparatus for detecting insulation failure in a machine is disclosed. The machine includes an input duct for receiving a cooling gas, a gas mixture region producing a mixed gas including the cooling gas and gas produced by the thermal decomposition of insulation within the machine, and an output duct for discharging the mixed gas. A first gas sample is obtained near the input duct and a second gas sample is obtained near the output duct. An analyzer is employed to assess the difference between the first sample and the second sample. This assessment detects potential thermal decomposition of the insulation within the machine. If thermal decomposition is present, a warning signal is provided.

6 Claims, 3 Drawing Sheets

OVERHEATED ELECTRICAL INSULATION DETECTOR

BACKGROUND OF THE INVENTION

Detection of insulation overheating is of great importance and interest to both manufacturers and users of any equipment which utilizes electrical insulation. It is of particular interest for applications in rotating machinery because of inherent difficulties detecting overheating of insulation combined with the need to know the condition of the insulation in order to interrupt the operation of the machine before catastrophic damage occurs. Due to the harsh environment existing inside rotating machines and difficulties of measuring insulation condition directly, no reliable prior art method exist for non-intrusive monitoring of the bulk insulation, particularly for detection of overheating.

Many prior art electrical rotating machines, such as electric motors, are cooled by forcing air flow or other media (hydrogen, for example) through the motor. If atmospheric air is used as the media the exhaust is usually discharged into the surrounding environment.

As typical electrical insulating materials are heated above normal temperatures, for example, by localized currents due to insulation failure, localized heating results. Under these circumstances large amounts of gases are released. Such releases begin at a relatively low temperature, generally prior to extensive damage to the machine. If these gas releases can be identified using early detection technique it is possible to de-energize the machine before extensive damage, such as extensive conductor melting, occurs.

However, in the absence of the use of early detection techniques, such as the technique disclosed by this patent application, such localized heating frequently results in severe damage to the machine before these currents are detected and interrupted by conventional circuit breakers. Typical damage includes severe melting of electrical conductors.

The preferred embodiment of the invention comprises a pump to sample differentially the cooling gases at the input and exhaust ducts of the machine, sensors to detect the presence in the cooling gases of products produced when insulation overheats, a data system, a control system, means to analyze the data and means to initiate appropriate action when insulation overheating is detected.

Sensors of the type used in the invention are subject to considerable drift. Additionally the ambient environment in which electrical equipment may normally be operated may contain significant amounts of the gases of the type that are released as the insulation overheats. These factors are compensated for in order to detect the actual breakdown of the insulation, as more specifically described below.

Typical electrical insulating material (epoxy, for example) generates a wide variety of gases including carbon monoxide and hydrocarbons as a result of thermal breakdown. These gases are readily detected using commercially available metal oxide semiconductor (MOS) reducing gas sensors. Variations in sensor characteristics, such as variations in sensitivity among sensors to a specific change and changes in sensitivity with time are compensated for to substantially reduce the adverse impact of sensor characteristics on the detection process.

Typical values for gaseous materials produced as insulation thermally decomposes (under a certain set of conditions) are shown in the following chart.

TABLE 1

| Epoxy Insulation Thermal Decomposition Products | | | | | | | |
|---|---|---|---|---|---|---|---|
| Temperature °C. | 130 | 150 | 195 | 195 | 225 | 245 | 290 |
| Carbon Monoxide | 630 | 474 | 1120 | 396 | 916 | 11690 | 39260 |
| Carbon Dioxide | 1340 | 1260 | 2410 | 2480 | 2480 | 25820 | 47300 |
| Methane | 18 | 14 | 19 | 7 | 30 | 338 | 1000 |
| Acetylene | 0 | 0 | 0 | 0 | 0 | 14 | 50 |
| Ethylene | 10 | 0 | 17 | 0 | 59 | 533 | 1030 |
| Ethane | 0 | 0 | 0 | 0 | 0 | 39 | 90 |
| Propane | 27 | 14 | 34 | 11 | 37 | 170 | 230 |
| Butylene | 0 | 0 | 0 | 0 | 0 | 0 | 0 |
| Butane | 0 | 0 | 0 | 0 | 0 | 0 | 0 |

All values are in microliters/liters ($\mu L/L$)

Many of the gases released as insulation thermally decomposes are also present in the environment. Additionally, as discussed above, currently available MOS reducing gas sensors are subject to variations in sensitivity and long term drift. These factors are compensated for in two complementary ways.

First, advantage is taken of the fact that the process of thermal breakdown of insulation is very rapid in rotating machines, resulting in rapid changes in the concentration of breakdown products in the cooling gas. Changes in the concentration of these gases in the environment are typically slow, permitting environmental changes over the detection interval to be ignored. Secondly, a differential technique is used to compare the concentration of products contained in the cooling gas flowing in the exhaust duct of the equipment being monitored to the concentration of products contained in the gas flowing in the input duct to compensate for slow environmental changes in gases which are detected by the sensors (and thus the ambient gases). These two techniques overcome sensor drift, differing sensor sensitivity and changes in the ambient environment.

Selected gaseous products previously discussed, are produced at relatively low temperatures, thus permitting detection of insulation deteriorations before extensive machine damage occurs. This non-intrusive technique was specifically developed for early detection of overheated insulation in the stator, rotor and core insulation systems in a wide variety of air cooled electric motors and electric generators. It can also be used to detect abnormal conditions in any other equipment provided the abnormal condition results in the release of gases which are detectable by the sensor.

SUMMARY OF THE INVENTION

The apparatus comprising the invention monitors the cooling exhaust (cooling air) from a machine and senses the presence of gases characteristic of thermal breakdown of insulation. Carbon monoxide and carbon dioxide are released in considerable quantities at temperatures as low as 150° C. and as the temperature is increased above 200° C., a variety of other gases including hydrocarbons is also released.

Unlike hydrocarbons, carbon monoxide is not present in insulation systems or in high concentrations in the environment. The system and method which is the subject matter of the disclosed invention monitors the combination of carbon monoxide and hydrocarbons in the exhaust gas to detect thermal decomposition of insulation.

Specifically, the preferred embodiment comprises a method and apparatus for early detection of thermal breakdown of insulation. In typical applications cooling air is drawn by a fan through the cooling air input duct, flows through the machine and over the insulation being monitored and out a cooling air exhaust duct. The cooling air is selectively and differentially sampled at the input duct and at the exhaust duct of the machine being monitored to produce samples of the cooling gas. These samples are analyzed to detect thermal breakdown of insulation based on the composition of the samples, specifically changes in the concentration of carbon monoxide and hydrocarbons.

This sampling technique is useful because the sensor responds to changes in the concentration of gases in the environment which may be significantly changed by such factors as smoking, welding, internal combustion engine operation and oil contamination of the premises. A sampling period is selected which is short compared to the expected rate of change in the concentration of these gases due to environmental causes. Additionally, this process is differential in nature permitting variations in characteristics to be compensated for.

DETAILED DESCRIPTION

Figure 1:
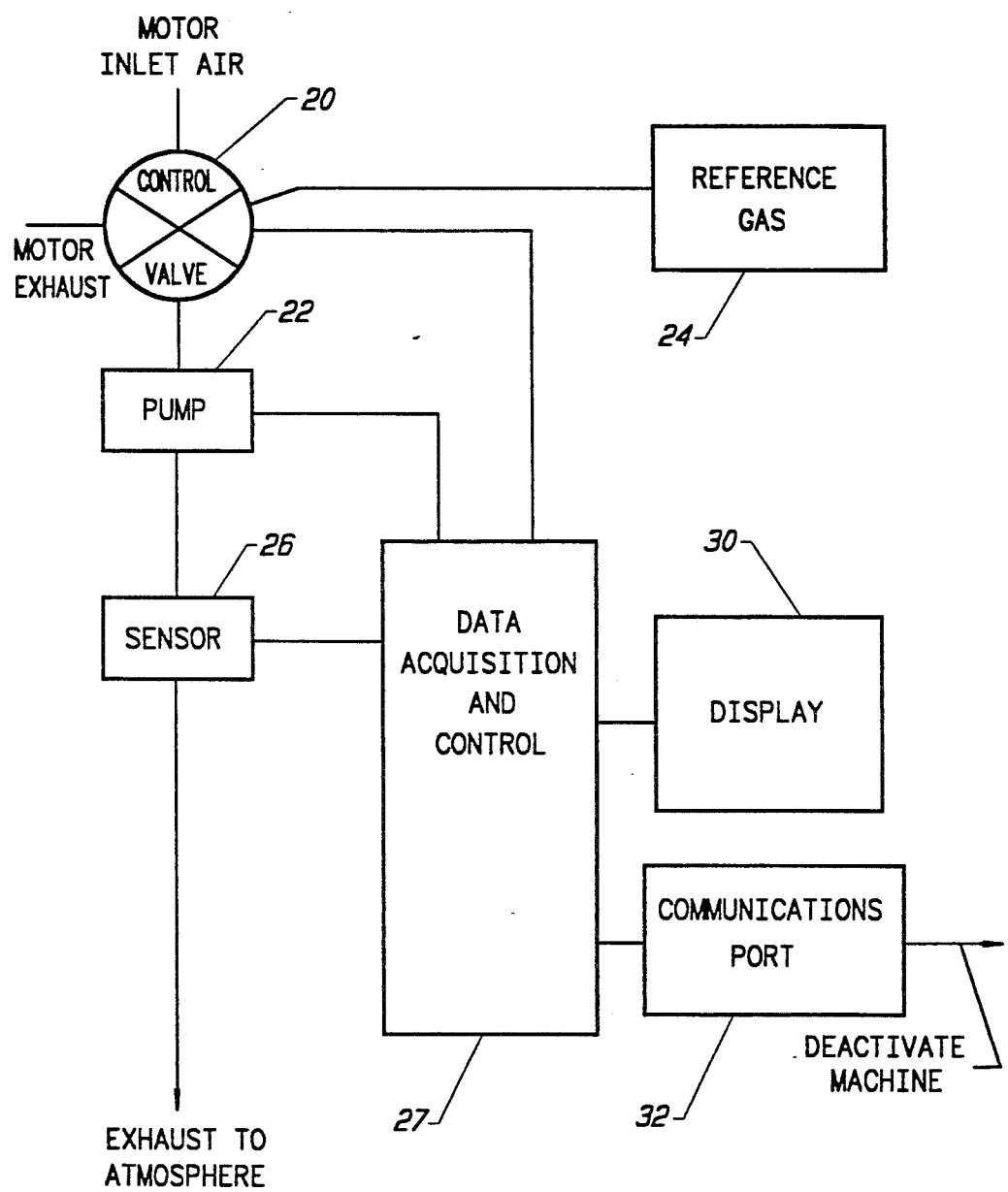
FIG. 1 is a schematic diagram of the apparatus comprising the preferred embodiment of the invention.

FIG. 1 is a functional block diagram illustrating the apparatus comprising the preferred embodiment of the invention. A three way valve 20 selectively couples the input of a pump 22 to sample the cooling air at the inlet of the cooling air duct to a machine, at the exhaust of the cooling air duct of the machine and a reference gas supplied by a reference gas source 24.

A sensor 26 is coupled to receive the output of the pump 22 and produce signals having a predetermined relationship to the amounts and/or composition of the gas samples flowing through the sensor 26. Gases flowing through the sensor 26 are discharged into the atmosphere.

Operation of the system is coordinated by a data acquisition and control system 27, which may be a properly programmed digital computer coupled to other apparatus comprising the system through suitable interfaces. A suitable display unit 30 provides a convenient visual indication of the test results. Additionally, a communications, e.g., RS 32 port provides means to interface the system with control apparatus to initiate an alarm and/or turn off the machine to prevent further damage.

The preferred sensor is a commercially available MOS reducing gas sensor. In the preferred embodiment the three way valve 20 is also selectively positioned by the data acquisition and control system 27 to cause the reference gas to flow through the sensor 26. This permits the data acquisition system to produce reference signals related to known gases to check the long term stability of the system and to assure that the system is functional. In other positions gas from the cooling air inlet duct and the exhaust duct are directed to the sensor 26, as described above.

Figure 2:
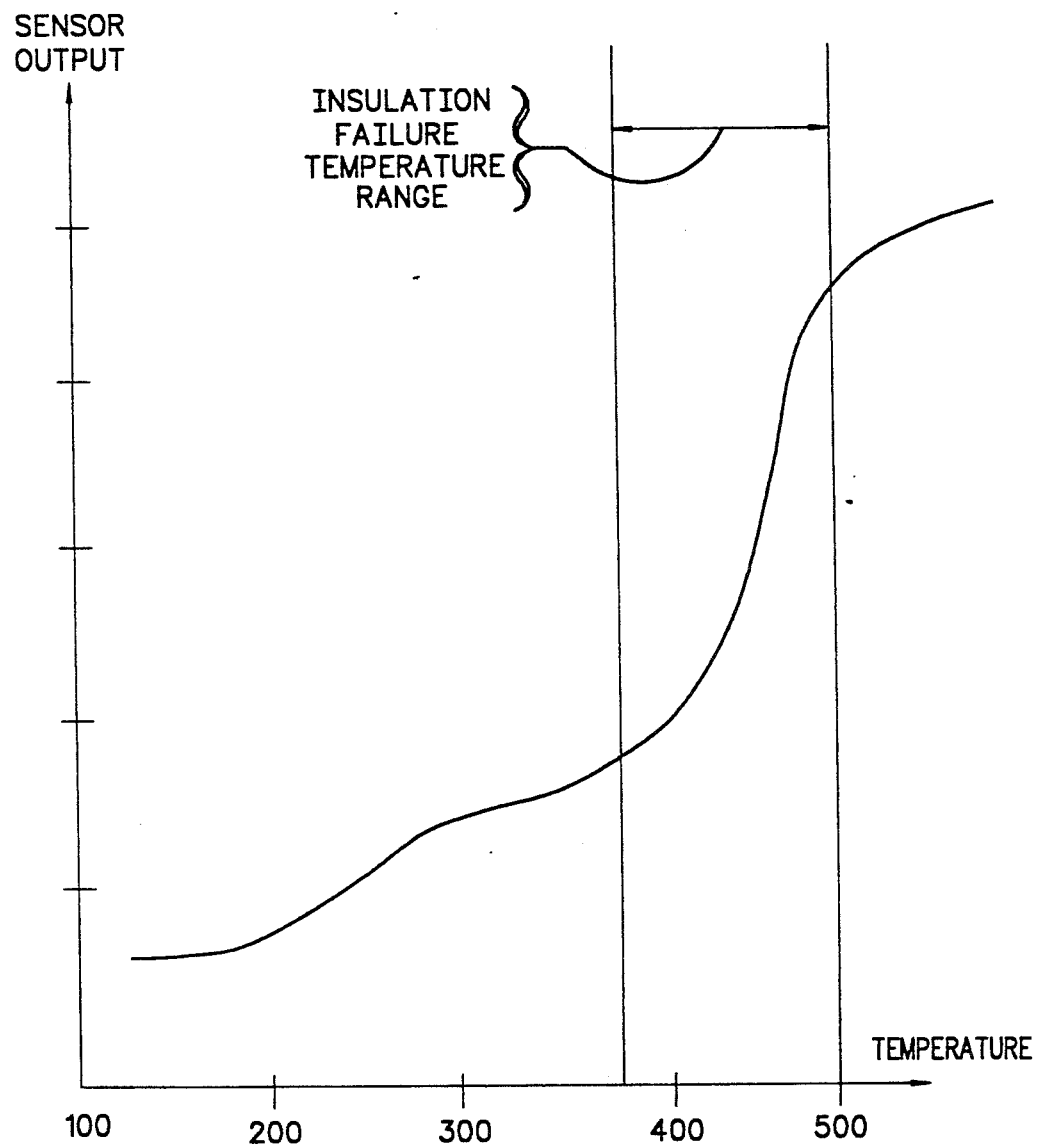
FIG. 2 is a graph illustrating the response of a typical sensor of the type used by the invention to gases produced as insulation thermally decomposes.

FIG. 2 illustrates a typical response of the MOS reducing gas sensor to typical gases generated as insulation thermally breaks down as a function of insulation temperature. The response of the sensor in the range of 100° C. is partially due to hydrocarbons and other gases present in the environment. As can be seen from this illustration, significant changes in the output of the sensor due to thermal decomposition of insulation occurs at a temperature as low as 200° C. If the machine can be de-energized before the insulation exceeds a temperature in the range of 200° to 500° C. severe damage to the conductors is usually prevented. Preventing serious damage to the conductors significantly reduces repair cost.

Figure 3:
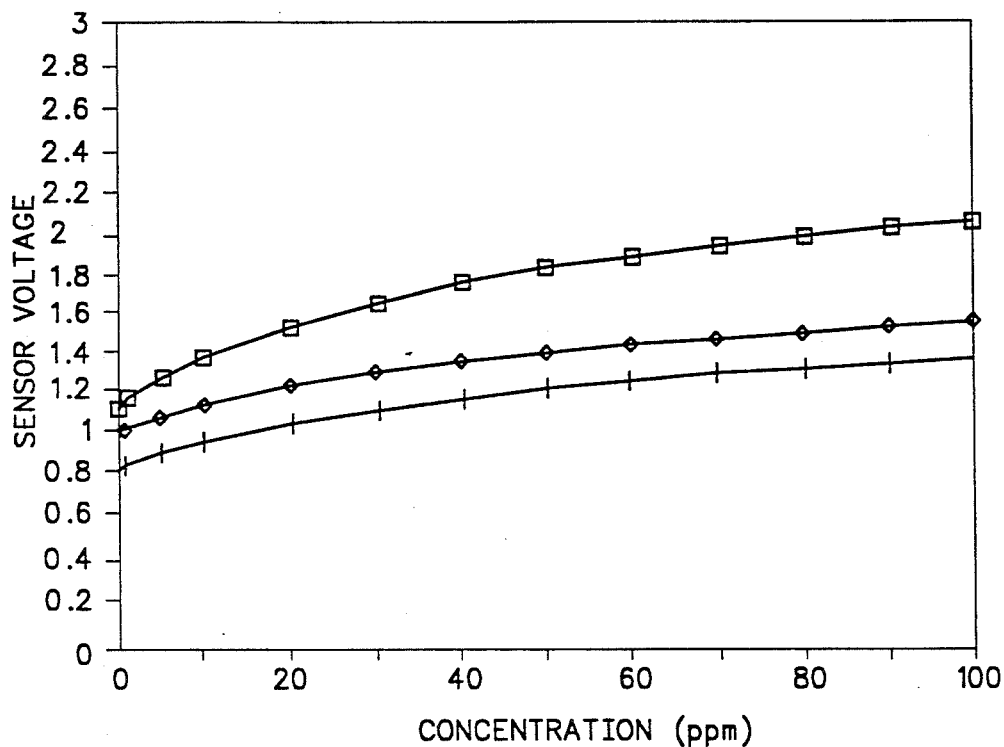
FIG. 3 is a curve illustrating the differential response of a sensor of the type used in the invention to samples of the cooling air in the inlet duct and to samples of the air in the exhaust duct as a function of the insulation temperature.

Sensors of the type used in the invention also vary widely as to sensitivity to the gases released as the temperature of the insulation is increased. The sensitivity of three typical sensors is illustrated in FIG. 3 as a function of gas concentration. As will be obvious to those skilled in the art, sensitivity curves of this type clearly illustrate that the increase in gas concentration as a result of thermal breakdown of insulation can not be reliably detected by a sensor of this type based on the absolute value of the sensor output signal. That is, any system utilizing these sensors must compensate for differences between individual sensors. Additionally, long term drift in the output of currently available MOS reducing gas sensors is significant. However, differential techniques and rate of change of the output signal with respect to time, as utilized by the disclosed invention, can be used to reliably detect insulation breakdown, as fully discussed below.

Figure 4:
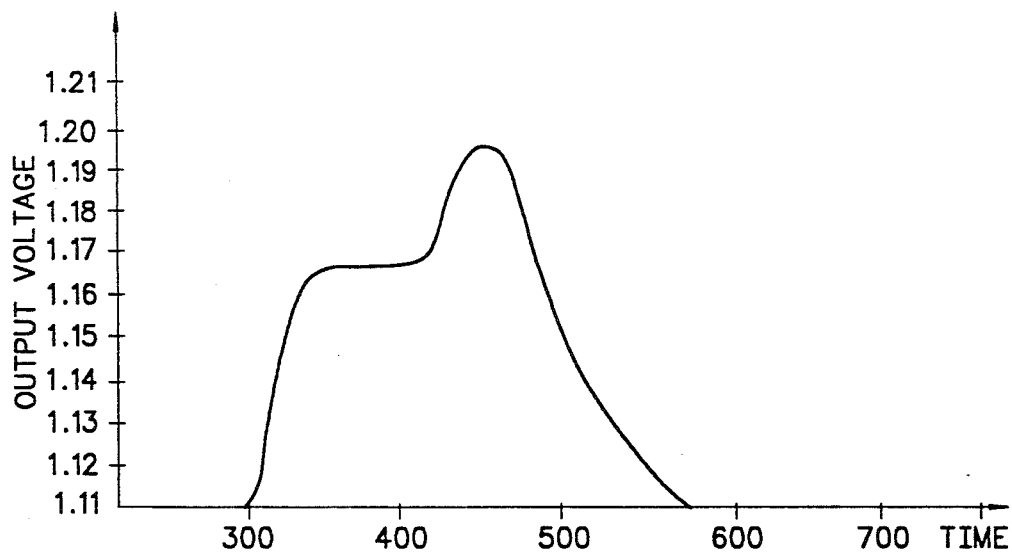
FIG. 4 is a drawing illustrating the differential response of the sensor to samples of the input and exhaust cooling air.

FIG. 4 is a diagram illustrating the operation of the system when the sensor is operated in the differential mode. As previously discussed, the data acquisition system operates the valve 20 to alternately sample the air in the cooling air input duct and in the cooling air exhaust duct. These samples are directed to flow through the sensor 26 with the output signal of the sensor 26 sampled and recorded. The responses of the sensor 26 to the samples of the gas in the input duct and in the exhaust duct are compared to produce a signal equal to the difference between these signals. FIG. 4 illustrates a typical result of this comparison. When this difference exceeds a predetermined level, an alarm is initiated and/or the machine being monitored is de-energized on the basis that the analysis of these gases indicates that insulation is thermally decomposing due to an increase in temperature. A typical threshold for disabling the machine is 1.16 volts in about 20 seconds using one particular kind of MOS sensor.

The various elements of the system are commercially available. Components other than those illustrated may be used provided the substituted components perform as required.

Many modifications of the disclosed system are possible. For example, if more stable and more sensitive sensors become available, it may be possible to detect overheating at an earlier stage. Sensors specific to carbon monoxide and hydrocarbons might reduce the concern about environmental changes in these gases. Changes to utilize these technical developments based for instance on multi-sensor arrangements are believed to be within the scope of this invention.

We claim:

1. A method of detecting insulation failure in a machine which includes an input duct for receiving a cooling gas, a gas mixture region producing a mixed gas comprising said cooling gas and gas produced by the thermal decomposition of said insulation of said machine, and an output duct for discharging said mixed gas, said method comprising the steps of:

obtaining a first sample of said cooling gas proximate to said input duct;

acquiring a second sample of said mixed gas proximate to said output duct; and analyzing the difference between said first sample and said second sample to detect said thermal decomposition of said insulation of said machine.

2. The method of claim 1 further comprising the step of generating a warning signal in response to said analyzing step, said warning signal indicating the thermal decomposition of said insulation of said machine.

3. The method of claim 2 wherein said obtaining step and said acquiring step utilize a MOS gas sensor to generator said first sample and said second sample.

4. A machine with thermally decomposable insulation comprising:

an input duct for receiving a cooling gas;

a gas mixture region producing a mixed gas including said cooling gas and gas produced by the thermal decomposition of said thermally decomposable insulation of said machine;

an output duct for discharging said mixed gas;

means for obtaining a first sample of said cooling gas proximate to said input duct;

means for acquiring a second sample of said mixed gas proximate to said output duct; and means for analyzing the difference between said first sample and said second sample to detect said thermal decomposition of said insulation of said machine.

5. The apparatus of claim 4 further comprising means for generating a warning signal in response to said analyzing means, said warning signal indicating the thermal decomposition of said insulation of said machine.

6. The apparatus of claim 5 wherein said means for obtaining and said means for acquiring utilize a MOS gas sensor to generate said first sample and said second sample.

* * * * *